(12) United States Patent
Wynne et al.

(10) Patent No.: US 6,949,563 B2
(45) Date of Patent: Sep. 27, 2005

(54) (2-CARBOXAMIDO)(3-AMINO)THIOPHENE COMPOUNDS

(76) Inventors: Graham Michael Wynne, 15 Larkspur Square, Bicester, Oxfordshire, OX26 3WL (GB); Kevin Doyle, 9 Mullein Road, Bicester, Bicester, Oxfordshire OX263WE (GB); Saleh Ahmed, 31 Dudley Street, Belgreen, Coventry, CV67EE (GB); An-Hu Li, 25 N. Clinton Ave., Apt.# 4B, Bay Shore, NY (US) 11706; John Fraser Keily, 16 Prestwich Road, Oxford, Oxfordshire, OX20ED (GB); Chrystelle Marie Rasamison, 140 Magdalen Road, Cowley, Oxford OX41RL (GB); Neil Anthony Pegg, 14 Aris Way, Buckingham MK181FX (GB); Imaad Saba, 40 Swinburne Road, Oxford, OX44BG (GB); Claire Thomas, 26 Crompton Way, Newland, Whitney, OX283AB (GB); Don Smyth, 72 Mergancer Drive, Bicester, OX266UG (GB); Shazia Sadiq, 24 Three Corners Road, Northfields, Oxford, OX37UE (GB); Gary Newton, Flat 8, 105 Oxford Rd., Cowley, Oxford, Oxfordshire, OX42ER (GB); Graham Dawson, 74 Foster Road, Abingdon, Oxfordshire, OX141YW (GB); Andrew Phillip Crew, 1677 August Rd., North Babylon, NY (US) 11703; Arlindo Lucas Castelhano, Apt. 1677, Somerset Village, New City, NY (US) 11703

( * ) Notice: Subject to any disclaimer, the term of this patent is extended or adjusted under 35 U.S.C. 154(b) by 0 days.

(21) Appl. No.: 10/752,342

(22) Filed: Jan. 6, 2004

(65) Prior Publication Data

US 2004/0186124 A1 Sep. 23, 2004

Related U.S. Application Data

(60) Provisional application No. 60/526,358, filed on Dec. 2, 2003, provisional application No. 60/524,972, filed on Nov. 25, 2003, and provisional application No. 60/438,152, filed on Jan. 6, 2003.

(51) Int. Cl.[7] .............. A61K 31/4745; A61K 31/4709; A61K 31/4436; A61K 31/381; C07D 49/02
(52) U.S. Cl. ............. 514/300; 514/311; 514/314; 514/354; 514/422; 514/446; 546/113; 546/152; 546/176; 546/280.4; 549/65
(58) Field of Search ............... 546/152, 280.4, 546/113, 176; 514/311, 354, 300, 314, 422, 446; 549/65

(56) References Cited

U.S. PATENT DOCUMENTS 5,968,965 A  10/1999  Dinsmore et al. .......... 514/399

(Continued)

FOREIGN PATENT DOCUMENTS

| EP | 0 832 061 | 4/1998 |
|---|---|---|
| WO | WO 99/032477 | 7/1999 |

(Continued)

OTHER PUBLICATIONS

Lala, P.K. et al., Cancer and Metastasis Reviews (1998), 17(1), 91–106.*

(Continued)

*Primary Examiner*—Joseph K. McKane
*Assistant Examiner*—Susannah E. Lee
(74) *Attorney, Agent, or Firm*—Alexander Stewart; Shu M. Lee

(57) ABSTRACT

Compounds represented by Formula (I):

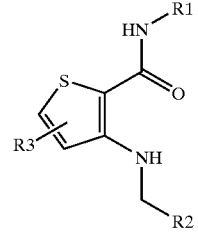

or a pharmaceutically acceptable salt or N-oxide thereof, wherein R1 is

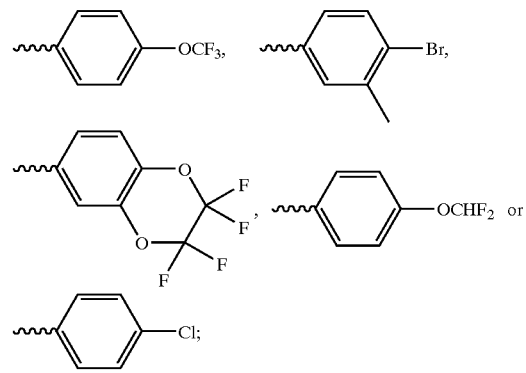

R2 is

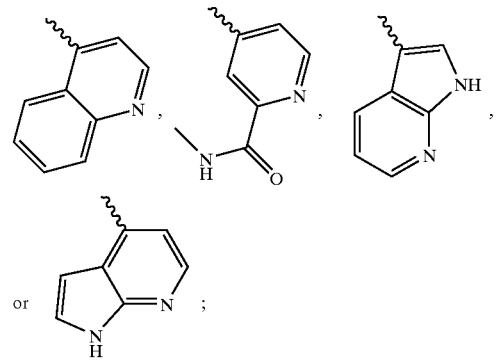

and R3 is $C_{0-4}$alkyl, are useful in the treatment of cancer.

16 Claims, No Drawings

U.S. PATENT DOCUMENTS

| | | | |
|---|---|---|---|
| 6,140,351 A | 10/2000 | Arnaiz et al. | 514/336 |
| 6,187,799 B1 * | 2/2001 | Wood et al. | 514/363 |
| 6,207,693 B1 | 3/2001 | Setoi et al. | 514/394 |
| 6,316,482 B1 | 11/2001 | Setoi et al. | 514/394 |
| 6,376,515 B2 | 4/2002 | Zhu et al. | 514/318 |
| 6,410,561 B1 | 6/2002 | Shinkai et al. | 514/313 |
| 6,448,277 B2 | 9/2002 | Altmann et al. | 514/357 |

FOREIGN PATENT DOCUMENTS

| | | |
|---|---|---|
| WO | WO 00/027819 | 5/2000 |
| WO | WO 00/027820 | 5/2000 |
| WO | WO 02/066470 | 8/2000 |
| WO | WO 01/05763 | 1/2001 |
| WO | WO 01/007050 | 2/2001 |
| WO | WO 01/019798 | 3/2001 |
| WO | WO 01/064642 | 9/2001 |
| WO | WO 02/000651 | 1/2002 |
| WO | WO 02/055501 | 7/2002 |
| WO | WO 02/068406 | 9/2002 |

OTHER PUBLICATIONS

Golub, T.R. et al., Science (1999), vol. 286, 531–537.*
Sihto, Harri et al., "KIT and Platlet–Derived Growth Factor Receptor Alpha Tyrosine Kinase Gene Mutations and KIT Amplifications in Human Solid Tumors," Journal of Clinical Oncology, vol. 23(1), 2005, pp. 49–57.
Potti, Anil et al., "Immunohistochemical Determination of HER–2/neu Overexpression in Malignant Melanoma Reveals No Prognostic Value, while c–KIT Overexpression Exhibits Potential Therapeutic Implications," Journal of Carcinogenesis, vol. 2(8), 2003.

* cited by examiner

(2-CARBOXAMIDO)(3-AMINO)THIOPHENE COMPOUNDS

This application claims the benefit of Provisional application Ser. Nos. 60/438,152, filed Jan. 6, 2003, 60/524,972, filed Nov. 25, 2003, and 60/526,358, filed Dec. 2, 2003.

BACKGROUND OF THE INVENTION

The present invention is directed to 2,3-substituted thiophenes. In particular, the present invention is directed to (2-carboxamido)(3-amino)thiophenes that are inhibitors of c-Kit proto-oncogene (also known as Kit, CD-117, stem cell factor receptor, mast cell growth factor receptor).

The c-Kit proto-oncogene is believed to be important in embryogenesis, melanogenesis, hematopoiesis, and the pathogenesis of mastocytosis, gastrointestinal tumors, and other solid tumors, as well as certain leukemias, including AML. Accordingly, it would be desirable to develop novel compounds that are inhibitors of the c-Kit receptor.

Many of the current treatment regimes for hyperproliferative disorders (cancer) utilize compounds that inhibit DNA synthesis. Such compounds' mechanism of operation is to be toxic to cells, particularly to rapidly dividing tumor cells. Thus, their broad toxicity can be a problem to the subject patient. However, other approaches to anti-cancer agents that act other than by the inhibition of DNA synthesis have been explored to try to enhance the selectivity of the anti-cancer action and thereby reduce adverse side-effects.

It is known that a cell may become cancerous by virtue of the transformation of a portion of its DNA into an oncogene (i.e. a gene which, on activation, leads to the formation of malignant tumor cells). Many oncogenes encode proteins that are aberrant protein-tyrosine kinases capable of causing cell transformation. By a different route, the overexpression of a normal proto-oncogenic tyrosine kinase can also result in proliferative disorders, sometimes resulting in a malignant phenotype. Alternatively, co-expression of a receptor tyrosine kinase and its cognate ligand within the same cell type may also lead to malignant transformation.

Receptor tyrosine kinases are large enzymes which span the cell membrane and possess i) an extracellular binding domain for growth factors such as KIT ligand (also known as stem cell factor (SCF), Steel factor (SLF) or mast cell growth factor (MGF)), ii) a transmembrane domain, and iii) an intracellular portion which functions as a kinase to phosphorylate specific tyrosine residues in proteins. Binding of KIT ligand to KIT tyrosine kinase results in receptor homodimerization, the activation of KIT tyrosine kinase activity, and the subsequent phosphorylation of a variety of protein substrates, many of which are effectors of intracellular signal transduction, These events can lead to enhanced cell proliferation or promote enhanced cell survival. With some receptor kinases, receptor heterodimerization can also occur.

It is known that such kinases are frequently aberrantly expressed in common human cancers such as breast cancer, head and neck cancers, gastrointestinal cancer such as colon, rectal or stomach cancer, leukemia, and ovarian, bronchial, lung or pancreatic cancer. Kit kinase expression has been documented in a wide variety of human malignancies such as mastocytosis/mast cell leukemia, gastrointestinal stromal tumors (GIST), small cell lung carcinoma (SCLC), sinonasal natural killer/T-cell lymphoma, testicular cancer (seminoma), thyroid carcinoma, malignant melanoma, ovarian carcinoma, adenoid cystic carcinoma, acute myelogenous leukemia (AML), breast carcinoma, pediatric T-cell acute lymphoblastic leukemia, angiosarcoma, anaplastic large cell lymphoma, endometrial carcinoma, and prostate carcinoma. The kinase activity of KIT has been implicated in the pathophysiology of several of these—and additional tumors—including breast carcinoma, SCLC, GIST, germ cell tumors, mast cell leukemia, neuroblastoma, AML, melanoma and ovarian carcinoma.

Several mechanisms of KIT activation in tumor cells have been reported, including activating mutations, autocrine and paracrine activation of the receptor kinase by its ligand, loss of protein-tyrosine phosphatase activity, and cross activation by other kinases. The transforming mechanisms initiated by the activating mutations are thought to include dimer formation and increased intrinsic activity of the kinase domain, both of which result in constitutive ligand-independent kinase activation, and possibly altered substrate specificity. More than thirty activating mutations of the Kit protein have been associated with highly malignant tumors in humans.

Accordingly, it has been recognized that inhibitors of receptor tyrosine kinases are useful as selective inhibitors of the growth of mammalian cancer cells. For example, Gleevec™ (also known as imatinib mesylate, or STI571), a 2-phenylpyrimidine tyrosine kinase inhibitor that inhibits the kinase activity of the BCR-ABL fusion gene product, was recently approved by the U.S. Food and Drug Administration for the treatment of CML. Gleevec™, in addition to inhibiting BCR-ABL kinase, also inhibits the KIT kinase and PDGF receptor kinase, although it is not effective against all mutant isoforms of the KIT kinase. Kit ligand-stimulated growth of MO7e human leukemia cells is inhibited by Gleevec™, which also induces apoptosis under these conditions. By contrast, GM-CSF stimulated growth of MO7e human leukemia cells is not affected by Gleevec™. Further, in recent clinical studies using Gleevec™ to treat patients with GIST, a disease in which KIT kinase is involved in transformation of the cells, many of the patients showed marked improvement.

These studies demonstrate how KIT kinase inhibitors can treat tumors whose growth is dependent on KIT kinase activity. Other kinase inhibitors show even greater kinase selectivity. For example, the 4-anilinoquinazoline compound Tarceva™ inhibits only EGF receptor kinase with high potency, although it can inhibit the signal transduction of other receptor kinases, probably by virtue of the fact that these receptors heterodimerize with EGF receptor.

Although anti-cancer compounds such as those described above make a significant contribution to the art, there is a continuing need for improved anti-cancer pharmaceuticals, and it would be desirable to develop new compounds with better selectivity or potency, or with reduced toxicity or side effects.

International Patent Publication No. WO00/27820 describes N-aryl(thio)anthranilic acid amide derivatives. International Patent Publication No. WO99/32477 and U.S. Pat. No. 6,140,351 describe ortho-anthranilimide derivatives. International Patent Publication No. WO00/27819 describes anthranilic acid amides. International Patent Publication Nos. WO02/00651 and WO01/19798 describe factor Xa inhibitors. International Patent Publication No. WO01/07050 describes nociceptin receptor ORL-1 agonists. U.S. Pat. No. 5,968,965 describes farnesyl-protein inhibitors. International Patent Publication No. WO01/64642 and U.S. Pat. No. 6,376,515 describe benzamides. International Patent Publication No. WO01/05763 and U.S. Pat. No. 6,410,561 describe muscarinic receptor active compounds. U.S. Pat. No. 6,410,561 describes amide derivatives.

International Patent Publication No. WO02/066470 describes substituted alkylamine derivatives. International Patent Publication No. WO02/068406 describes substituted amine derivatives International Patent Publication No. WO02/055501 describes substituted arylamine derivatives.

U.S. Pat. Nos. 6,207,693 and 6,316,482, and European Patent No. EP0832061 describe benzamide derivatives having vasopressin antagonistic activity.

SUMMARY OF THE INVENTION

Compounds represented by Formula (I):

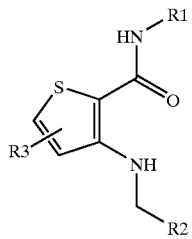
(I)

or a pharmaceutically acceptable salt or N-oxide thereof, wherein R1 is

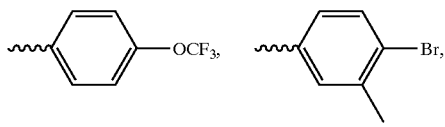

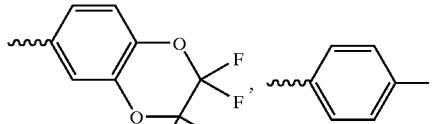

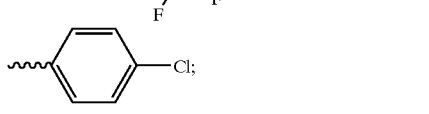

R2 is

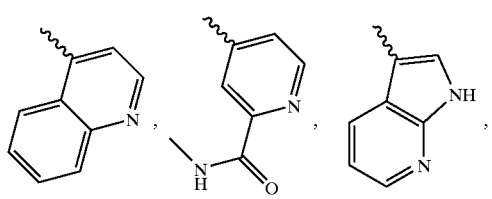

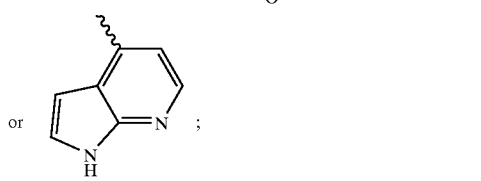

and R3 is $C_{0-4}$alkyl, are useful in the treatment of tumors.

DETAILED DESCRIPTION OF THE INVENTION

The present invention is directed to a compound represented by Formula (I):

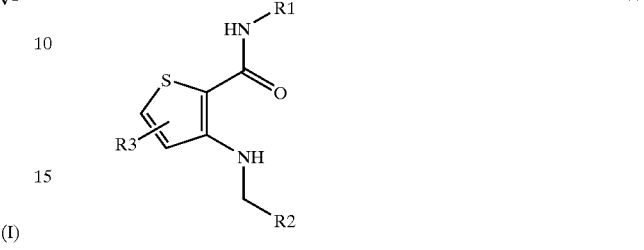
(I)

or a pharmaceutically acceptable salt or N-oxide thereof, wherein

R1 is

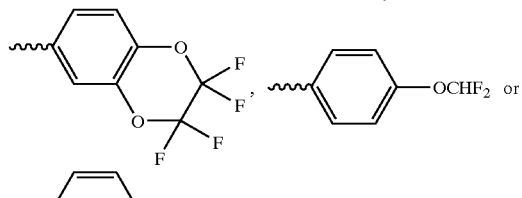

R2 is

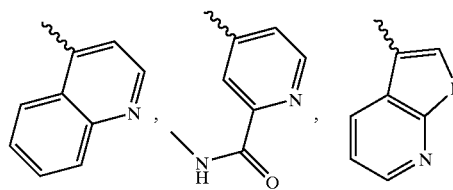

or 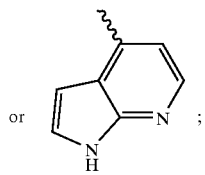

and

R3 is $C_{0-4}$alkyl.

In one aspect, the present invention is directed to a compound represented by Formula (I), or a pharmaceutically acceptable salt or N-oxide thereof, wherein R2 is

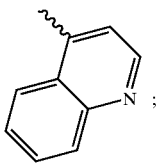

and the other variables are as described above for Formula (I).

In one embodiment of this one aspect, the present invention is directed to a compound represented by Formula (I), or a pharmaceutically acceptable salt or N-oxide thereof, wherein R2 is

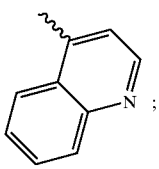

R3 is hydrogen; and the other variables are as described above for Formula (I).

In a second aspect, the present invention is directed to a compound represented by Formula (I), or a pharmaceutically acceptable salt or N-oxide thereof, wherein R2 is

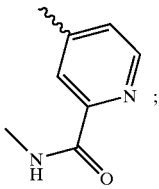

R3 is $C_{0-4}$alkyl; and the other variables are as described above for Formula (I).

In an embodiment of this second aspect, the present invention is directed to a compound represented by Formula (I), or a pharmaceutically acceptable salt or N-oxide thereof wherein R2 is

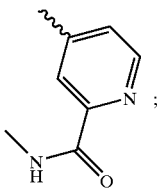

R3 is hydrogen; and the other variables are as described above for Formula (I).

In a third aspect, the present invention is directed to a compound represented by Formula (I), or a pharmaceutically acceptable salt or N-oxide thereof, wherein R2 is

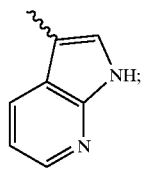

R3 is $C_{0-4}$alkyl; and the other variables are as described above for Formula (I).

In an embodiment of this third aspect, the present invention is directed to a compound represented by Formula (I), or a pharmaceutically acceptable salt or N-oxide thereof, wherein R2 is

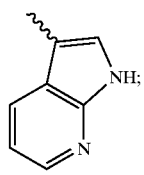

R3 is hydrogen; and the other variables are as described above for Formula (I).

In a fourth aspect, the present invention is directed to a compound represented by Formula (I), or a pharmaceutically acceptable salt or N-oxide thereof, wherein R2 is

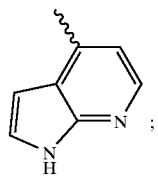

R3 is $C_{0-4}$alkyl; and the other variables are as described above for Formula (I).

The present invention is also directed to a method of treating hyperproliferative disorders, including breast cancer, head cancer, or neck cancer, gastrointestinal cancer, leukemia, ovarian, bronchial, lung, or pancreatic cancer, sinonasal natural killer/T-cell lymphoma, testicular cancer (seminoma), thyroid carcinoma, malignant melanoma, adenoid cystic carcinoma, angiosarcoma, anaplastic large cell lymphoma, endometrial carcinoma, or prostate carcinoma, by administering an effective amount of a compound represented by Formula II, or a pharmaceutically acceptable salt thereof:

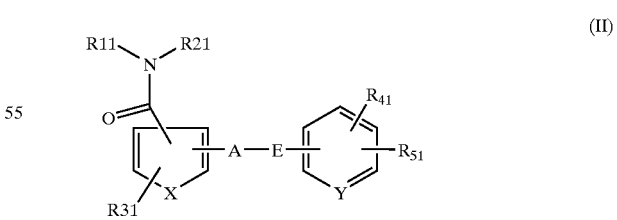

(II)

wherein:

R11 is aryl, $C_{3-6}$cycloalkyl or heterocyclyl, each of which optionally is substituted with 1–6 independent halogen; hydroxy; nitro; amino; acyl; substituted acyl; acyl$C_{1-6}$ alkylsulfinyl; acyl$C_{1-6}$alkylsulfonyl; acyloxy; $C_{1-6}$alkylamino$C_{1-6}$alkyl carbamoyloxy; aryl; cyano; heterocyclyl; $C_{2-6}$alkenyl optionally substituted with acyl, substituted acyl, aryl or acyl-substituted aryl; $C_{2-6}$alkynyl optionally substituted with amino, acylamino or substituted acylamino; $C_{1-6}$alkyl optionally substituted with halogen, amino, $C_{1-6}$alkylamino, acylamino, substituted acylamino, hydroxy, acyloxy, acyl$C_{1-6}$alkanoyloxy, acyl, substituted acyl, acyl$C_{1-6}$alkoxyimino, aryl or acyl substituted aryl; $C_{1-6}$alkylthio optionally substituted with acyl or substituted acyl; alkoxy optionally substituted with aryl, substituted aryl, hydroxy, acyloxy, amino, lower alkylamino, protected amino, heterocyclyl, acyl substituted pyridyl, substituted acyl substituted pyridyl, halogen, acyl$C_{1-6}$alkylamino, N-protected acyl$C_{1-6}$alkylamino, N-acyl$C_{1-6}$alkyl-N-lower alkylamino, acyl, substituted acyl, acylamino, substituted acylamino, $C_{1-6}$alkylhydrazinocarbonylamino, hydroxyimino, acyl$C_{1-6}$alkoxyimino, substituted acyl$C_{1-6}$alkoxyimino, acyl$C_{1-6}$alkoxy, guanidino or N-protected guanidino; or $C_{2-6}$alkenyloxy optionally substituted with acyl or substituted acyl substituents;

R21 is hydrogen; lower alkyl optionally substituted with hydroxy, aryl or acyl; or cyclo(lower)alkyl;

R31 is hydrogen; halogen; hydroxy; acyloxy; substituted acyloxy; $C_{1-6}$alkyl optionally substituted with hydroxy or $C_{1-6}$alkoxy; $C_{1-6}$alkoxy optionally substituted with aryl, amino, protected amino, acyl, hydroxy, cyano or $C_{1-6}$alkylthio; nitro; amino; acyl; substituted acyl; or $C_{3-6}$cycloalkyloxy;

$R_{41}$ is hydroxy; halogen; nitro; amino; protected amino; $C_{1-6}$alkylamino; acyloxy; amino$C_{1-6}$alkylamino; N-protected amino$C_{1-6}$alkylamino; $C_{1-6}$alkoxy optionally substituted with hydroxy, aryl, substituted aryl, acyl, substituted acyl, amino, $C_{1-6}$alkylamino, acylamino, substituted acylamino, protected amino, heterocyclyl or guanidino; $C_{1-6}$alkylthio optionally substituted with acyl, substituted acyl, amino, $C_{1-6}$alkylamino, acylamino, substituted acylamino, protected amino, heterocyclyl, hydroxy, $C_{1-6}$alkylsulfonyloxy, arylsulfonyloxy, ar$C_{1-6}$alkoxy or substituted ar$C_{1-6}$alkoxy; $C_{1-6}$alkyl substituted with acyl, substituted acyl, amino, lower alkylamino, acylamino, substituted acylamino, protected amino, heterocyclyl, hydroxy, $C_{1-6}$alkylsulfonyloxy or arylsulfonyloxy; $C_{2-6}$alkenyl optionally substituted with acyl; $C_{2-6}$alkynyl optionally substituted with hydroxy, amino, protected amino, $C_{1-6}$alkylsulfonyloxy or arylsulfonyloxy; amino$C_{1-6}$alkylsulfonyl; N-protected amino$C_{1-6}$alkylsulfonyl; $C_{1-6}$alkylaminosulfonyl; heterocyclylsulfonyl; amino$C_{1-6}$alkylsulfinyl; N-protected amino$C_{1-6}$alkylsulfinyl; piperidyloxy; or N-protected piperidyloxy;

$R_{51}$ is hydrogen, $C_{1-6}$alkyl, $C_{1-6}$alkoxy or halogen;

A is a single bond, O or NH;

E is $C_{1-6}$alkylene, $C_{2-6}$alkenylene,

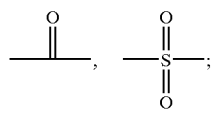

or E is a group of the formula —G—J— in which
G is $C_{1-6}$alkylene and
J is O or

wherein $R_{61}$ is hydrogen or N-protective group;
X is —CH=CH—, —C=N— or S; and
Y is CH or N.

Compounds of Formula (II) are described in U.S. Pat. No. 6,054,457.

In one aspect, the present invention is directed to a method of treating hyperproliferative disorders, including breast cancer, head cancer, or neck cancer, gastrointestinal cancer, leukemia, ovarian, bronchial, lung, or pancreatic cancer, sinonasal natural killer/T-cell lymphoma, testicular cancer (seminoma), thyroid carcinoma, malignant melanoma, adenoid cystic carcinoma, angiosarcoma, anaplastic large cell lymphoma, endometrial carcinoma, or prostate carcinoma, by administering an effective amount of a compound represented by Formula II, or a pharmaceutically acceptable salt thereof, wherein X is S, and the other variables are as described above for Formula II.

In an embodiment of this aspect, the present invention is directed to a method of treating hyperproliferative disorders, including breast cancer, head cancer, or neck cancer, gastrointestinal cancer, leukemia, ovarian, bronchial, lung, or pancreatic cancer, sinonasal natural killer/T-cell lymphoma, testicular cancer (seminoma), thyroid carcinoma, malignant melanoma, adenoid cystic carcinoma, angiosarcoma, anaplastic large cell lymphoma, endometrial carcinoma, or prostate carcinoma, by administering an effective amount of a compound represented by Formula II, or a pharmaceutically acceptable salt thereof, wherein X is S: R11 is optionally substituted aryl; and the other variables are as described above for Formula II.

In another embodiment of this aspect, the present invention is directed to a method of treating hyperproliferative disorders, including breast cancer, head cancer, or neck cancer, gastrointestinal cancer, leukemia, ovarian, bronchial, lung, or pancreatic cancer, sinonasal natural killer/T-cell lymphoma, testicular cancer (seminoma), thyroid carcinoma, malignant melanoma, adenoid cystic carcinoma, angiosarcoma, anaplastic large cell lymphoma, endometrial carcinoma, or prostate carcinoma, by administering an effective amount of a compound represented by Formula II, or a pharmaceutically acceptable salt thereof, wherein X is S; R11 is optionally substituted heterocyclyl; and the other variables are as described above for Formula II.

In still another embodiment of this aspect, the present invention is directed to a method of treating hyperproliferative disorders, including breast cancer, head cancer, or neck cancer, gastrointestinal cancer, leukemia, ovarian, bronchial, lung, or pancreatic cancer, sinonasal natural killer/T-cell lymphoma, testicular cancer (seminoma), thyroid carcinoma, malignant melanoma, adenoid cystic carcinoma, angiosarcoma, anaplastic large cell lymphoma, endometrial carcinoma, or prostate carcinoma, by administering an effective amount of a compound represented by Formula II, or a pharmaceutically acceptable salt thereof, wherein X is S, Y is N, and the other variables are as described above for Formula II.

The present invention is also directed to a method of treating hyperproliferative disorders, including breast cancer, head cancer, or neck cancer, gastrointestinal cancer, leukemia, ovarian, bronchial, lung, or pancreatic cancer, sinonasal natural killer/T-cell lymphoma, testicular cancer (seminoma), thyroid carcinoma, malignant melanoma, adenoid cystic carcinoma, angiosarcoma, anaplastic large cell lymphoma, endometrial carcinoma, or prostate carcinoma, by administering an effective amount of a compound represented by Formula III:

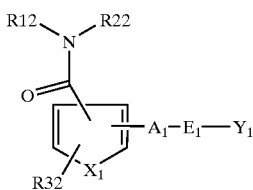 (III)

wherein:

R12 is aryl, $C_{3-6}$cycloalkyl or heterocyclyl, each of which optionally is substituted with 1–6 independent halogen; hydroxy; nitro; protected amino, amino; acyl; substituted acyl; acyl$C_{1-6}$alkylsulfinyl; acyl$C_{1-6}$alkylsulfonyl; acyloxy; $C_{1-6}$alkylamino$C_{1-6}$alkyl carbamoyloxy; aryl; cyano; heterocyclyl; $C_{2-6}$alkenyl optionally substituted with acyl, substituted acyl, aryl or acyl-substituted aryl; $C_{2-6}$alkynyl optionally substituted with amino, acylamino or substituted acylamino; $C_{1-6}$alkyl optionally substituted with halogen, amino, $C_{1-6}$alkylamino, acylamino, substituted acylamino, hydroxy, acyloxy, acyl$C_{1-6}$alkanoyloxy, acyl, substituted acyl, acyl$C_{1-6}$alkoxyimino, aryl or acyl substituted aryl; $C_{1-6}$alkylthio optionally substituted with acyl or substituted acyl; alkoxy optionally substituted with aryl, substituted aryl, hydroxy, acyloxy, amino, lower alkylamino, protected amino, heterocyclyl, acyl substituted pyridyl, substituted acyl substituted pyridyl, halogen, acyl$C_{1-6}$alkylamino, N-protected acyl$C_{1-6}$alkylamino, N-acyl$C_{1-6}$alkyl-N-lower alkylamino, acyl, substituted acyl, acylamino, substituted acylamino, $C_{1-6}$alkylhydrazinocarbonylamino, hydroxyimino, acyl$C_{1-6}$alkoxyimino, substituted acyl$C_{1-6}$alkoxyimino, acyl$C_{1-6}$alkoxy, guanidino or N-protected guanidino; or $C_{2-6}$alkenyloxy optionally substituted with acyl or substituted acyl substituents;

R22 is hydrogen; $C_{1-6}$alkyl optionally substituted with hydroxy, aryl or acyl; or $C_{3-6}$cycloalkyl;

R32 is hydrogen; halogen; hydroxy; acyloxy; substituted acyloxy; $C_{1-6}$alkyl optionally substituted with hydroxy or $C_{1-6}$alkoxy; $C_{1-6}$alkoxy optionally substituted with aryl, amino, protected amino, acyl, hydroxy, cyano or $C_{1-6}$alkylthio; nitro; amino; acyl; substituted acyl; or $C_{3-6}$cycloalkyloxy;

$A_1$ is a single bond, O, or NH;

$E_1$ is $C_{1-6}$alkylene, $C_{2-6}$alkenylene,

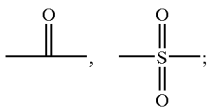

or $E_1$ is a group of the formula —G1-J1- in which
G1 is $C_{1-6}$alkylene or

and
J1 is O or

wherein $R_{62}$ is hydrogen or N-protective group;

$X_1$ is —CH═CH—, —C═N— or S; and $Y_1$ is aryl optionally substituted with 1–6 independent acyl, protected amino$C_{1-6}$alkanoyl, protected amino and nitro, amino and nitro or diamino substituents; or Y1 is a condensed heterocyclyl optionally substituted with 1–6 halogen, acyl, $C_{1-6}$alkoxy, hydroxy, guanidino, mercapto, acylamino, amino, heterocyclyl, cyanoamino, amino$C_{1-6}$alkyl($C_{1-6}$alkyl)amino, $C_{1-6}$alkylamino, $C_{1-6}$alkylamino ($C_{1-6}$alkylamino), substituted heterocyclyl, $C_{1-6}$alkylhydrazino, aryloxy, $C_{1-6}$alkylthio, aryl, protected amino, N-protected $C_{1-6}$alkylamino($C_{1-6}$alkyl)amino, N-protected amino$C_{1-6}$alkyl(N'—$C_{1-6}$alkyl)amino, amino$C_{1-6}$alkyl(N—$C_{1-6}$alkyl)amino, $C_{1-6}$alkylamino($C_{1-6}$alkyl)(N—$C_{1-6}$alkyl)amino, or $C_{1-6}$alkoxy($C_{1-6}$alkyl)amino substituents, or a $C_{1-6}$alkyl substituent further optionally substituted with aryl, ar$C_{1-6}$alkoxy, cyano, hydroxyimino, mercapto, $C_{1-6}$alkylamino, acyloxy, halogen, $C_{1-6}$alkoxy, protected hydroxy, hydroxy, $C_{1-6}$alkoxyaryl, protected amino, amino, heterocyclyl, or substituted heterocyclyl sub-substituents;

provided that when $Y_1$ is phenyl optionally substituted with $C_{1-6}$alkyl or acyl, then
$A_1$ is a single bond, and
$E_1$ is

Compounds of Formula (III) are described in U.S. Pat. No. 6,316,482.

In one aspect, the present invention is directed to a method of treating hyperproliferative disorders, including breast cancer, head cancer, or neck cancer, gastrointestinal cancer, leukemia, ovarian, bronchial, lung, or pancreatic cancer, sinonasal natural killer/T-cell lymphoma, testicular cancer (seminoma), thyroid carcinoma, malignant melanoma, adenoid cystic carcinoma, angiosarcoma, anaplastic large cell lymphoma, endometrial carcinoma, or prostate carcinoma, by administering an effective amount of a compound represented by Formula III, or a pharmaceutically acceptable salt thereof, wherein $X_1$ is S, and the other variables are as described above for Formula III.

As used herein, "$C_{0-4}$alkyl" is used to mean an alkyl having 0–4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

As used herein unless otherwise specified, "alkyl", "alkenyl", and "alkynyl" includes straight or branched configurations. Lower alkyls, alkenyls, and alkynyls have 1–6 carbons. Higher alkyls, alkenyls, and alkynyls have more than 6 carbons.

As used herein unless otherwise specified, the terms "aryl" and "ar" are well known to chemists and include, for example, phenyl and naphthyl, as well as phenyl with one or more short alkyl groups (tolyl, xylyl, mesityl, cumenyl, di(t-butyl)phenyl). Phenyl, naphthyl, tolyl, and xylyl are preferred. "Substituted aryl" is an aryl substituted with suitable substituents such as, for example, acyl, substituted acyl, N-protected piperazinylsulfonyl, piperazinylsulfonyl, N—$C_{1-6}$alkylpiperazinylsulfonyl, hydroxy$C_{1-6}$alkyl, heterocyclyl, halogen, nitro, amino, $C_{1-6}$alkylamino, cyano, or $C_{1-6}$alkoxy.

As used herein unless otherwise specified, "heterocyclyl" is well known to chemists and contains at least one N, S or O hetero-ring atom, and includes saturated, unsaturated, partially saturated, mono or polycyclic heterocyclic groups such as, for example, pyrrolyl, pyrrolinyl, imidazoylyl, pyrazolyl, pyridyl, pyrimidinyl, pyrazinyl, pyridazinyl, triazolyl, tetrazolyl, pyrrolidinyl, imidazolidinyl, piperidyl, piperazinyl, homopiperazinyl, indolyl, isoindolyl, indolizinyl, benzimidazolyl, quinolyl, isoquinolyl, imidazopyridyl, indazolyl, benzotriazolyl, tetrazolopyridazinyl, pyranyl, furyl, 1H-tetrahydropyranyl, tetrahydrofuranyl, thienyl, oxazolyl, isoxazolyl, oxadiazoyl, oxazolinyl, morpholinyl, benzofuranyl, benzoxazolyl, benzoxadiazolyl, thiazolyl, thiadiazolyl, thiazolidinyl, benzothiazolyl, benzothiadiazolyl, benzofuranyl, or benzodioxyl and the like. Such heterocyclyls are suitably substituted with lower alkyl or oxo substituents.

As used herein unless otherwise specified, "acyl" includes for example, carboxy, esterified carboxy, carbamoyl, lower alkylcarbamoyl, lower alkanoyl, aroyl, heterocyclylcarbonyl, and the like. Esterified carboxy includes substituted or unsubstituted lower alkoxycarbonyl such as methoxycarbonyl, ethoxycarbonyl, propoxycarbonyl, butoxycarbonyl, t-butoxycarbonyl, hexyloxycarbonyl, 2-iodoethoxycarbonyl, 2,2,2-trichloroethoxycarbonyl, dimethylaminopropoxycarbonyl, dimethylaminoethoxycarbonyl; substituted or unsubstituted aryloxycarbonyl such as phenoxycarbonyl, 4-nitrophenoxycarbonyl, 2-naphthyloxycarbonyl; substituted or unsubstituted ar(lower)alkoxycarbonyl such as benzyloxycarbonyl, phenethyloxycarbonyl, benzhydryloxycarbonyl, 4-nitrobenzyloxycarbonyl, 3-methoxy-4-nitrobenzyloxycarbonyl; and N-containing heterocyclyloxycarbonyl such as N-methylpiperidyloxycarbonyl and the like.

As used herein unless otherwise specified, "halogen" is fluorine, chlorine, bromine or iodine.

As used herein unless otherwise specified, "$C_{1-6}$alkylhydrazino" may be 2-mono or 2,2-di($C_{1-6}$alkyl) hydrazino such as 2-methylhydrazino, 2,2-dimethylhydrazino, 2-ethylhydrazino, 2,2-diethylhydrazino, or the like.

As used herein unless otherwise specified, "$C_{1-6}$alkylamino$C_{1-6}$alkyl" includes, for example, methylaminomethyl, dimethylaminomethyl, dimethylaminoethyl or the like.

"$C_{1-6}$alkanoyl" includes substituted or unsubstituted alkanoyls such as formyl, acetyl, propionylo, butyryl, isobutyryl, valeryl, isovaleryl, pivaloyl, hexanoyl, trifluoroacetyl or the like.

"aroyl" includes benzoyl, naphthoyl, toluoyl, di(t-butyl) benzoyl and the like.

As used herein unless otherwise specified, "N-protective group" in "protected amino", includes substituted or unsubstituted lower alkanyl (such as, for example, formyl, acetyl, propionyl, trifluoroacetyl), phthaloyl, lower alkoxycarbonyl (such as t-butoxycarbonyl, t-amyloxycarbonyl), substituted or unsubstituted aralkyloxycarbonyl (such as benzyloxycarbonyl, p-nitrobenzyloxycarbonyl), 9-fluorenylmethoxycarbonyl, substituted or unsubstituted arenesulfonyl(benzenesulfonyl, tosyl). Phthaloyl, t-butoxycarbonyl or 9-fluorenylmethoxycarbonyl are preferred.

As used herein unless otherwise specified, "N-protective group" in "protected guanidino", includes lower alkoxycarbonyl (such as t-butoxycarbonyl, t-amyloxycarbonyl).

As used herein unless otherwise specified, "hydroxy-protective group" includes substituted or unsubstituted arylmethyl (for example, benzyl, lower alkoxybenzyl), acyl, or substituted silyl (for example, t-butyldiphenylsilyl).

The above Formulas I, II, and III are shown without a definitive stereochemistry at certain positions. The present invention includes all stereoisomers of Formulas I, II, and III and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The invention also encompasses a pharmaceutical composition that is comprised of a compound of Formula I in combination with a pharmaceutically acceptable carrier.

Preferably, the composition is comprised of a pharmaceutically acceptable carrier and a non-toxic therapeutically effective amount of a compound of Formula I as described above (or a pharmaceutically acceptable salt or N-oxide thereof).

Moreover, within this preferred embodiment, the invention encompasses a pharmaceutical composition for the treatment of disease by the inhibition of the c-Kit kinase, which may be a wild-type or mutant form of the protein, comprising a pharmaceutically acceptable carrier and a non-toxic therapeutically effective amount of compound of Formula I as described above (or a pharmaceutically acceptable salt or N-oxide thereof).

The compounds and compositions of the present invention are effective for treating mammals such as, for example, humans.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, methanesulfonic, and tartaric acids.

The pharmaceutical compositions of the present invention or used by the methods of the present invention comprise a compound represented by Formula I, II, or III (or a pharmaceutically acceptable salt or N-oxide thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts or N-oxides thereof, of this invention can be combined as the active ingredient in intimate admixture with a pharmaceutical carrier according to conventional pharmaceutical compounding techniques. The carrier may take a wide variety of forms depending on the form of preparation desired for administration. E.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt or N-oxide thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt or N-oxide of Formula I, II, or III. The compounds of Formula I, II, or III, or pharmaceutically acceptable salts or N-oxides thereof, can also be included in pharmaceutical compositions in combination with one or more other therapeutically active compounds.

The pharmaceutical compositions of this invention include a pharmaceutically acceptable liposomal formulation containing a compound of Formula I, II, or III or a pharmaceutically acceptable salt or N-oxide thereof.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent or other such excipient. These excipients may be, for example, inert diluents such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer time. For example, a time delay material such as glyceryl monostearate or glyceryl distearate may be used.

In hard gelatin capsules, the active ingredient is mixed with an inert solid diluent, for example, calcium carbonate, calcium phosphate or kaolin. In soft gelatin capsules, the active ingredient is mixed with water or an oil medium, for example, peanut oil, liquid paraffin or olive oil. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material, which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt or N-oxide thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts or N-oxides thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 10 g per patient per day. For example, breast cancer, head and neck cancers, and gastrointestinal cancer such as colon, rectal or stomach cancer may be effectively treated by the administration of from about 0.01 to 100 mg of the compound per kilogram of body weight per day, or alternatively about 0.5 mg to about 7 g per patient per day.

Similarly, leukemia, ovarian, bronchial, lung, and pancreatic cancer may be effectively treated by the administration of from about 0.01 to 100 mg of the compound per kilogram of body weight per day, or alternatively about 0.5 mg to about 7 g per patient per day.

Mastocytosis/mast cell leukemia, gastrointestinal stromal tumors (GIST), small cell lung carcinoma (SCLC), sinonasal natural killer/T-cell lymphoma, testicular cancer (seminoma), thyroid carcinoma, malignant melanoma, ovarian carcinoma, adenoid cystic carcinoma, acute myelogenous leukemia (AML), breast carcinoma, pediatric T-cell acute lymphoblastic leukemia, angiosarcoma, anaplastic large cell lymphoma, endometrial carcinoma, and prostate carcinoma may be effectively treated by the administration of from about 0.01 to 100 mg of the compound per kilogram of body weight per day, or alternatively about 0.5 mg to about 7 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention, or pharmaceutically acceptable salts or N-oxides thereof, can also be effectively administered in conjunction with other cancer therapeutic compounds. For example, cytotoxic agents and angiogenesis inhibiting agents can be advantageous co-agents with the compounds of the present invention. Accordingly, the present invention includes compositions comprising the compounds represented by Formula I, or a pharmaceutically acceptable salt or N-oxide thereof, and a cytotoxic agent or an angiogenesis-inhibiting agent. The amounts of each can be therapeutically effective alone—in which case the additive effects can overcome cancers resistant to treatment by monotherapy. The amounts of any can also be subtherapeutic—to minimize adverse effects, particularly in sensitive patients.

It is understood that the treatment of cancer depends on the type of cancer. For example, lung cancer is treated differently as a first line therapy than are colon cancer or breast cancer treated. Even within lung cancer, for example, first line therapy is different from second line therapy, which in turn is different from third line therapy. Newly diagnosed patients might be treated with cisplatinum containing regimens. Were that to fail, they move onto a second line therapy such as a taxane. Finally, if that failed, they might get a tyrosine kinase EGFR inhibitor as a third line therapy. Further, The regulatory approval process differs from country to country. Accordingly, the accepted treatment regimens can differ from country to country. Nevertheless, the compounds of the present invention, or pharmaceutically acceptable salts or N-oxides thereof, can be beneficially co-administered in conjunction or combination with other such cancer therapeutic compounds. Such other compounds include, for example, a variety of cytotoxic agents (alkylators, DNA topoisomerase inhibitors, antimetabolites, tubulin binders); inhibitors of angiogenesis; and different other forms of therapies including kinase inhibitors such as Tarceva, monoclonal antibodies, and cancer vaccines. Other such compounds that can be beneficially co-administered with the compounds of the present invention include doxorubicin, vincristine, cisplatin, carboplatin, gemcitabine, and the taxanes. Thus, the compositions of the present invention include a compound according to Formula I, or a pharmaceutically acceptable salt or N-oxide thereof, and an anti-neoplastic, anti-tumor, anti-angiogenic, or chemotherapeutic agent.

The compounds of the present invention, or pharmaceutically acceptable salts or N-oxides thereof, can also be effectively administered in conjunction with other therapeutic compounds, aside from cancer therapy. For example, therapeutic agents effective to ameliorate adverse side-effects can be advantageous co-agents with the compounds of the present invention.

Representative EXAMPLES of the present invention are summarized in Table 1 below:

TABLE 1

| R1 | | | | |
|---|---|---|---|---|
| 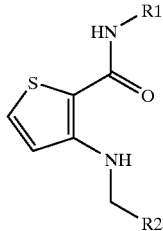 | 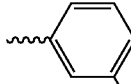 | 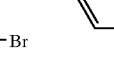 | 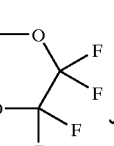 | 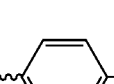 |
| R2 | Ex. 1 | Ex. 2 | Ex. 3 | Ex. 4 |
| 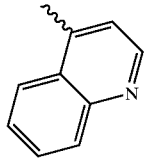 | Ex. 1 | Ex. 2 | Ex. 3 | Ex. 4 |
| 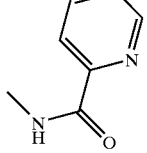 | Ex. 11 | Ex. 5 | Ex. 6 | Ex. 7 |
| 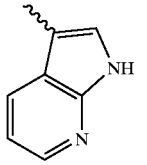 | Ex. 12 | Ex. 9 | Ex. 10 | Ex. 8 |

I. Activated c-Kit Kinase Bench Assay cDNA encoding the Kit tyrosine kinase domain was isolated from K562 cells and cloned into a baculovirus expression vector for protein expression as a fusion protein with GST (Glutathione S-Transferase) in insect cells. Following purification, the enzyme was incubated with ATP to generate a tyrosine phosphorylated, activated form of the enzyme, which was used in kinase assays to determine the ability of compounds to inhibit phosphorylation of an exogenous substrate by the Kit tyrosine kinase domain.

Phosphorylation of c-Kit Protein
The reagents used were as follows:
Column Buffer:
50 mM HEPES pH 7.4 125 mM NaCl
10% Glycerol
1 mg/mL BSA
2 mM DTT
200 μM NaVO$_3$
Phosphorylation Buffer:
50 mM HEPES pH 7.4
125 mM NaCl
24 mM MgCl$_2$
1 mM MnCl$_2$
1% Glycerol
200 μM NaVO$_3$
2 mM DTT
2 mM ATP 75 μL purified GST-Kit tyrosine kinase protein (approximately 150 μg) is incubated with 225 μL phosphorylation buffer for 1 h at 30° C. In a cold room, a desalting column (e.g. Pharmacia PD-10 column) is equilibrated using 25 mL of column buffer. Phosphorylated protein is applied to the column followed by sufficient column buffer to equal 2.5 mL total (in this case 2.2 mL). The phosphorylated Kit protein is then eluted with 3.5 mL column buffer, and collected into a tube containing 3.5 mL glycerol (final concentration of 50% glycerol). After mixing, aliquots are stored at −20° C. or −70° C.

Assay of c-Kit Kinase Activity

Kinase activity is determined in an ELISA-based assay that measures the ability of Kit to phosphorylate an exogenous substrate (poly Glu:Tyr) on tyrosine residues in the presence of ATP. Substrate phosphorylation is monitored by quantitation of the degree of binding of an antibody that recognizes only the phosphorylated tyrosine residues within the substrate following incubation with Kit. The antibody used has a reporter enzyme (e.g. horseradish peroxidase, HRP) covalently attached, such that binding of antibody to the phosphorylated substrate can be determined quantitatively by incubation with an appropriate HRP substrate (e.g. ABTS).

The stock reagents used are as follows:
13.3 μg/mL PGT stock solution: Add 66.7 μL 10 mg/mL PGT to 50 mL PBS.
1× wash buffer: Dilute 20× wash buffer (KPL #50-63-00) to 1× with H$_2$O.
Assay Buffer:
50 mM Hepes, pH 7.4
125 mM NaCl
24 mM MgCl$_2$ 1 mM MnCl$_2$
1% Glycerol
200 μM Vanadate—add immediately prior to use
2 mM DTT—add immediately prior to use
Assay buffer+ATP: Add 5.8 μL of 75 mM ATP to 12 mL of assay buffer.
Activated GST-c-kit(TK): Dilute 1:500 in assay buffer.
Block Buffer:
PBS containing 0.5% Tween-20, 3% BSA
200 μM Vanadate—add immediately prior to use
pY20-HRP:
Add 6.2 μL of a 100 μg/mL stock of pY20-HRP to 10 mL of block buffer
ABTS substrate: KPL 3 50-66-06, use as provided
Assay Protocol
Each well of a 94-well immulon-4 microtitre plate is coated with 75 μL of 13.3 μg/mL PGT stock solution, incubated overnight at 37° C. and washed once with 250 μL 1× wash buffer.

To the negative control wells, 50 μL of assay buffer (without ATP) are added, all other wells contain 50 μL assay buffer+ATP. To positive and negative control wells, 10 μL 5% DMSO is added, other wells contain 10 μL of test compounds (at concentrations between 10 nM and 100 μM) dissolved in 5% DMSO.

30 μL of activated GST-c-kit are added to initiate the assay, which is incubated at RT for 30 min, and then stopped by the addition of 50 μL/well of 0.5M EDTA. The plate is washed 3× with 1× wash buffer, and then 75 μL of a phospho-tyrosine-specific antibody-HRP conjugate (e.g. pY20-HRP, Calbiochem) in block buffer are added. The plate is incubated at RT for 2 h, and then washed 3× with 1× wash buffer. 100 μL of ABTS substrate are then added, the plate is incubated at RT for 30 min, and the reaction stopped by the addition of 100 μL of 1% SDS. The reaction is quantitated by measuring the OD at 405/490 nM on a microtitre plate reader.

Comparison of the assay signals obtained in the presence of compound with those of controls (in the presence and absence of ATP, with no compound added), allows the degree of inhibition of kinase activity to be determined over a range of compound concentrations. These inhibition values are fitted to a sigmoidal dose-response inhibition curve to determine the IC$_{50}$ values (i.e. the concentration of compound that reduces the kinase activity to 50% of the control activity).

The compounds of this invention reduced the ability of Kit to phosphorylate poly(Glu:Tyr) in the above assay, thus demonstrating direct inhibition of the c-Kit receptor tyrosine kinase activity. IC$_{50}$ values in this assay were between 9 nM and 388 nM.

The compounds of the present invention surprisingly and unexpectedly demonstrated better activity inhibiting c-Kit according to the above assay than the nearest similar thiophene compounds in the art (IC$_{50}$ values in this assay of the compounds of this invention were less than the IC$_{50}$ values in this assay of the known nearest thiophene compounds). Further, the compounds of the present invention surprisingly and unexpectedly are more stable chemically than many of their respective regioisomers.

Experimental

The EXAMPLES of the present invention were prepared according to the following procedures:

Referring to the scheme shown below for EXAMPLE 1, anilides of type 3 may be prepared directly from esters such as compound 1 under Weinreb amidation conditions, whereby said esters are reacted with anilines as exemplified by compound 2 in the presence of alkyl aluminum reagents such as (but not limited to) trimethylaluminum or chlorodimethylaluminum in a neutral solvent such as toluene or dichloromethane (*Synthetic Communications*, (1982), 12, 989).

Compounds such as 3 bearing a primary amino functionality may then be reacted with aldehydes under reducing conditions to give secondary amines such as EXAMPLE 1—for example in the presence of a mixture of triethylsilane and trifluoroacetic acid, or other reagents such as (but not limited to) sodium cyanoborohydride, sodium triacetoxyborohydride, sodium borohydride and hydrogen.

EXAMPLE 1

N-(4-trifluoromethoxyphenyl) 3-[(quinolin-4-ylmethyl)amino]thiophene-2-carboxamide

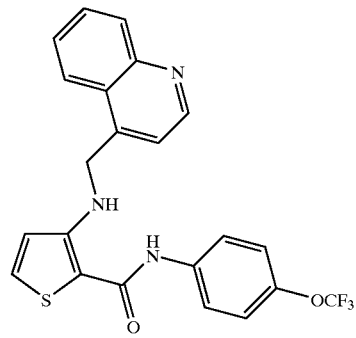

EXAMPLE 1 was prepared by the following procedure:

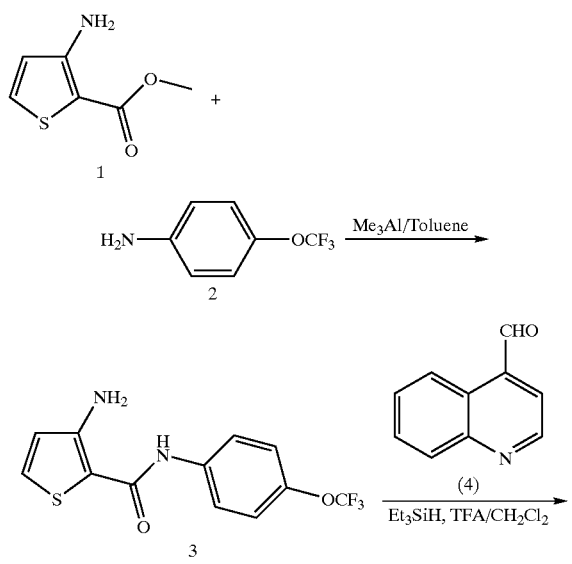

-continued

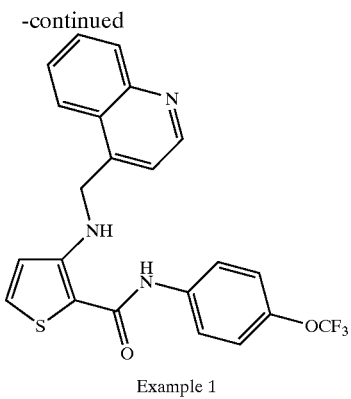

Example 1

Part 1:

N-(4-trifluoromethoxyphenyl) 3-Aminothiophene-2-carboxamide: To a stirred solution of 4-trifluoromethoxyaniline (7.8 g, 44.5 mmol) in toluene (50 mL) under nitrogen was added trimethylaluminum (2M in toluene, 26.7 mL, 53.4 mmol). The mixture was stirred at RT for 16 h. Methyl 3-amino-2-thiophenecarboxylate (7 g, 44.5 mmol) was added and the resulting solution was stirred at reflux (oil bath temperature: 130° C.) under nitrogen for 24 h. After cooling to RT, saturated sodium bicarbonate solution (100 mL) was added dropwise with caution and the mixture was stirred at RT for 30 min. The product was extracted into dichloromethane (3×100 mL), and the organic layer was dried over $Na_2SO_4$, and concentrated to yield a thick oil, which was then triturated with a mixture of hexane/ethyl acetate to afford N-(4-trifluoromethoxyphenyl) 3-Aminothiophene-2-carboxamide as a brown solid. $^1$H-NMR (400 MHz/$CD_3OD$): δ=6.65 (d, J=5.6 Hz, 1H), 7.23 (d, J=8.4 Hz, 2H), 7.39 (d, J=5.2 Hz, 1H), 7.67 (d, J=9.2 Hz, 2H). MS ($ES^+$): 303 [$MH^+$].

Part 2:

N-(4-trifluoromethoxyphenyl) 3-[(quinolin-4-ylmethyl)amino]thiophene-2-carboxamide: A solution of N-(4-trifluoromethoxyphenyl) 3-aminothiophene-2-carboxamide (1 g, 3.31 mmol) and quinoline-4-carboxaldehyde (347 mg, 2.21 mmol) in trifluoroacetic acid:dichloromethane (1:1, 30 mL) was heated at reflux for 2 h under nitrogen. The reaction was cooled to RT and triethylsilane (0.71 mL, 4.42 mmol) was added. The resulting solution was then stirred at reflux for 16 h under nitrogen. After cooling to RT, the reaction mixture was evaporated under reduced pressure and the residue was partitioned between ethyl acetate (3×100 mL) and saturated sodium bicarbonate solution (50 mL). The organic layers were dried over $Na_2SO_4$, filtered, and concentrated. The residue was purified by silica gel chromatography (20–30% ethyl acetate in hexane) to give EXAMPLE 1 as a light yellow solid, mp: 168–170° C. $^1$H-NMR (400 MHz/$CDCl_3$):δ=5.01 (d, J=6.2 Hz, 2H), 6.56 (d, J=5.4 Hz, 1H), 7.12 (s, 1H), 7.22 (d, J=8.7 Hz, 2H), 7.25 (s, 1H), 7.44 (d, J=4.3 Hz, 1H), 7.58 (d, J=9.0 Hz, 2H), 7.62 (t, J=8.2 Hz, 1H), 7.76 (t, J=8.3 Hz, 1H), 8.02 (d, J=7.5 Hz, 2H), 8.17 (d, J=8.3 Hz, 1H), 8.86 (d, J=4.5 Hz, 1H). MS ($ES^+$): 444 [$MH^+$]. $^{13}$C-NMR (400 MHz/$CDCl_3$): δ=45.9, 101.4, 117.9, 118.9, 119.5, 121.9, 122.0, 122.6, 126.5, 127.2, 129.1, 129.7, 130.6, 136.8, 144.5, 145.4, 148.3, 150.7, 155.9, 163.8. Anal. Calcd for $C_{22}H_{16}F_3N_3O_2S$: C, 59.59; H, 3.64; N, 9.48; F, 12.85; S, 7.23. Found: C, 59.59; H, 3.67; N, 9.46; F, 13.01; S, 7.23.

EXAMPLE 2

N-(4-bromo-3-methylphenyl) 3-[(Quinolin-4-ylmethyl)amino]thiophene-2-carboxamide EXAMPLE 2 was prepared according to the procedure described above for EXAMPLE 1, using 4-bromo-3-methylaniline instead of 4-trifluoromethoxyaniline. MS ($ES^+$): 452, 454 [$MH^+$]

EXAMPLE 3

N-(2,2,3,3-tetrafluorobenzodioxan-6-yl) 3-[(Quinolin-4-ylmethyl)amino]thiophene-2-carboxamide EXAMPLE 3 was prepared according to the procedure described above for EXAMPLE 1, using 6-amino-2,2,3,3-tetrafluorobenzodioxan instead of 4-trifluoromethoxyaniline. MS ($ES^+$): 490 [$MH^+$]

EXAMPLE 4

N-(4-chlorophenyl) 3-[(Quinolin-4-ylmethyl)amino]thiophene-2-carboxamide

EXAMPLE 4 was prepared according to the procedure described above for EXAMPLE 1, using 4-chloroaniline instead of 4-trifluoromethoxyaniline. MS ($ES^+$): 394, 396 [$MH^+$]

EXAMPLE 5

4-{[2-(4-Bromo-3-methylphenylcarbamoyl)thiophen-3-ylamino]methyl}pyridine-2-carboxylic acid methylamide To a stirred solution of N-(4-bromo-3-methylphenyl) 3-aminothiophene-2-carboxamide (1equiv, prepared as described above for EXAMPLE 1, part 1, using 4-bromo-3-methylaniline instead of 4-trifluoromethoxyaniline) in THF at 0° C. in an open flask, was added 2-(N-methylcarbamoyl)pyridine-4-carboxaldehyde (prepared as described in International Patent Publication No. WO 01/23375) (1.1equiv) in THF and 4M $H_2SO_4$ (0.1equiv) and the mixture was stirred for 30 min at 0° C. Sodium borohydride (1equiv) was added portionwise and the mixture was allowed to warm to RT and stirred for 2 h. Water was then added, the mixture was basified to pH 12 with 2M sodium hydroxide solution, and the resulting product was extracted into ethyl acetate. The combined extracts were washed with water followed by brine, dried ($MgSO_4$), filtered and concentrated in vacuo to afford a yellow semisolid, which was purified by column chromatography eluting with a 95:5 mixture of hexane:ethyl acetate increasing gradually to a 50:50 mixture. MS ($ES^+$): 459, 461 [$MH^+$]

EXAMPLE 6

4-{[2-(2,2,3,3-Tetrafluorobenzodioxan-6-ylcarbamoyl)thiophen-3-ylamino]methyl}pyridine-2-carboxylic acid methylamide EXAMPLE 6 was prepared according to the procedure described above for EXAMPLE 5, using N-(2,2,3,3-tetrafluorobenzodioxan-6-yl) 3-aminothiophene-2-carboxamide (prepared as described above for EXAMPLE 1, part 1, using 6-amino-2,2,3,3-tetrafluorobenzodioxan instead of 4-trifluoromethoxyaniline). MS ($ES^+$): 497 [$MH^+$]

EXAMPLE 7

4-{[2-(4-Chlorophenylcarbamoyl)thiophen-3-ylamino]methyl}pyridine-2-carboxylic acid methylamide EXAMPLE 7 was prepared according to the procedure described above for EXAMPLE 5, using N-(4- chlorophenyl) 3-aminothiophene-2-carboxamide (prepared as described above for EXAMPLE 1, part 1, using 4-chloroaniline instead of 4-trifluoromethoxyaniline). MS (ES$^+$): 401, 403 [MH$^+$]

EXAMPLE 8

N-(4-chlorophenyl) 3-[(1H-Pyrrolo[2,3-b]pyridin-3-ylmethyl)amino]thiophene-2-carboxamide Part 1:

7-Azaindole-3-carboxaldehyde: Phosphorus oxychloride (36.5 mL) was added dropwise to cooled solution of DMF (40 mL) while maintaining the temperature below 10° C. The resulting solution was further cooled to 5° C. and a solution of 7-azaindole in DMF (40 mL) was added slowly over 30–40 min, maintaining the temperature below 25° C. The mixture was heated at 95° C. for 48 h then cooled to 35° C. and added cautiously with stirring over an hour to a cooled solution of saturated aqueous sodium bicarbonate solution (800 mL). The mixture was extracted with ethyl acetate (4×500 mL) and the combined extracts washed with water (500 mL) and brine (500 mL), then dried (MgSO$_4$), filtered and concentrated in vacuo to afford a dark brown semi-solid. This crude product was purified using column chromatography eluting with a 50:50 mixture of ethyl acetate:hexane, gradually increasing to 90:10 mixture. 1H-NMR (400 MHz/D$_6$-DMSO): δ=7.25 (m, 1H), 8.38 (m, 2H), 8.42 (s, 1H), 9.92 (s, 1H), 12.62 (br.s, 1H). MS (ES$^+$): 147 [MH$^+$].

Part 2:

N-(4-chlorophenyl) 3-[(1H-Pyrrolo[2,3-b]pyridin-3-ylmethyl)amino]thiophene-2-carboxamide: Prepared according to the procedure described in EXAMPLE 5 using N-(4-chlorophenyl) 3-aminothiophene-2-carboxamide (prepared as described in EXAMPLE 1, part 1, using 4-chloroaniline instead of 4-trifluoromethoxyaniline) and 7-azaindole-3-carboxaldehyde (EXAMPLE 8, part 1) instead of 2-(N-methylcarbamoyl)pyridine-4-carboxaldehyde. MS (ES$^+$): 383, 385 [MH$^+$]

EXAMPLE 9

N-(4-bromo-3-methylphenyl) 3-[(1H-Pyrrolo[2,3-b]pyridin-3-ylmethyl)amino]thiophene-2-carboxamide EXAMPLE 9 was prepared according to the procedure described in EXAMPLE 5 using N-(4-bromo-3-methylphenyl) 3-aminothiophene-2-carboxamide (prepared as described in EXAMPLE 1, part 1, using 4-bromo-3-methylaniline instead of 4-trifluoromethoxyaniline) and 7-azaindole-3-carboxaldehyde (EXAMPLE 8, part 1) instead of 2-(N-methylcarbamoyl)pyridine-4-carboxaldehyde. MS (ES$^+$): 441, 443 [MH$^+$]

EXAMPLE 10

N-(2,2,3,3-tetrafluorobenzodioxan-6-yl) 3-[(1H-Pyrrolo[2,3-b]pyridin-3-ylmethyl)amino]thiophene-2-carboxamide EXAMPLE 10 was prepared according to the procedure described in EXAMPLE 5 using N-(2,2,3,3-tetrafluorobenzodioxan-6-yl) 3-aminothiophene-2-carboxamide (prepared as described in example 1 part 1, using 6-amino-2,2,3,3-tetrafluorobenzodioxan instead of 4-trifluoromethoxyaniline) and 7-azaindole-3-carboxaldehyde (EXAMPLE 8, part 1) instead of 2-(N-methylcarbamoyl)pyridine-4-carboxaldehyde. MS (ES$^+$): 479 [MH$^+$]

EXAMPLE 11

N-{[2-(4-Trifluoromethoxyphenylcarbamoyl)thiophen-3-ylamino]methyl}pyridine-2-carboxylic acid methylamide EXAMPLE 11 was prepared according to the procedure described above for EXAMPLE 5 using N-(4-trifluoromethoxyphenyl) 3-aminothiophene-2-carboxamide (prepared as described above for EXAMPLE 1). MS (ES$^+$): 451 [MH$^+$]

EXAMPLE 13

N-(4-Trifluoromethoxy)phenyl-3-[(1H-pyrrolo[2,3-b]pyridin-4-ylmethyl)amino]thiophene-2-carboxamide

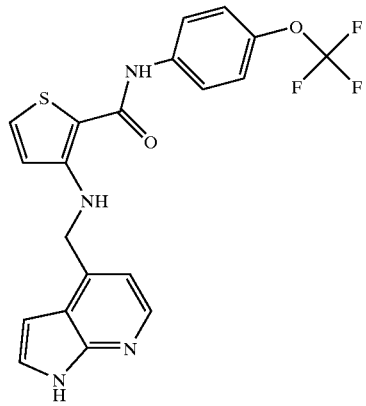

Part 1:

4-Chloro-1H-pyrrolo[2,3-b]pyridine: 1H-Pyrrolo[2,3-b]pyridine 7-oxide was added slowly to 200 mL POCl$_3$ and the resulting mixture stirred at 80° C. overnight. The excess POCl$_3$ was then removed in vacuo and the residue treated with 500 mL H$_2$O and basified with saturated K$_2$CO$_3$ (aq), prior to extraction with EtOAc (2×300 mL). The combined extracts were washed with water and brine, dried over anhydrous sodium sulfate and concentrated in vacuo to give 4-Chloro-1H-pyrrolo[2,3-b]pyridine (12.9 g, 76%). MS (ES+): 153 [MH$^+$].

Part 2:

4-Iodo-1H-pyrrolo[2,3-b]pyridine: To a solution of 4-Chloro-1H-pyrrolo[2,3-b]pyridine (12.9 g, 84.3 mmol) and NaI (40 g, 168 mmol) in acetonitrile (150 mL) was slowly added acetyl chloride (12.6 mL, 176 mmol). The mixture was allowed to stir at 80° C. for 4 days, and then the excess acetonitrile was removed in vacuo. 300 mL of 10% K$_2$CO$_3$ (aq) was added to the residue and the mixture extracted with CH$_2$Cl$_2$ (3×100 mL). The combined organic extracts were washed with 10% sodium bisulfite (aq) and brine, dried over anhydrous sodium sulfate and concentrated in vacuo to give crude product (22.2 g). To a solution of this crude product in THF (150 mL) was added 1M NaOH (100 mL). The mixture was stirred at room temperature for 2 hr prior to evaporation of the solvent in vacuo, dilution with water and extraction with $CH_2Cl_2$. The extracts were washed with brine, dried over anhydrous sodium sulfate and concentrated in vacuo. The resulting brown solid was purified by chromatography over silica gel and recrystallized from acetonitrile to give pure 4-Iodo-1H-pyrrolo[2,3-b]pyridine (9.75 g, 48%). MS (ES+): 245 [MH$^+$].

Part 3:

1H-Pyrrolo[2,3-b]pyridine-4-carbonitrile: To a solution of (4.7 g, 19.3 mmol) of 4-Iodo-1H-pyrrolo[2,3-b]pyridine in degassed DMF (25 mL) was added $Pd_2(dba)_3$ (10 mg), dppf (15 mg), degassed $H_2O$ (2 mL) and $Zn(CN)_2$ (1.4 g, 11.6 mmol). The mixture was stirred at 90° C. under nitrogen for 20 hr, then cooled to 70° C. and 75 mL of a 4:1:4 mixture of saturated $NH_4Cl:NH_4OH:H_2O$ was added. The mixture was stirred at 5° C. for 20 min. and the resulting precipitate filtered off, washed with 75 mL 4:1:5 mixture of saturated $NH_4Cl:NH_4OH:H_2O$, 500 mL $H_2O$ and 100 mL toluene, then dried in vacuo to give 2.06 g (74%) 1H-Pyrrolo[2,3-b]pyridine-4-carbonitrile. MS (ES+): 143 [MH$^+$]. $^1$H NMR (DMSO-$d_6$, 400 MHz): δ 6.65 (d, 1H, J=3.2), 7.56 (d, 1H, J=4.8 Hz), 7.84 (d, 1H, J=4.0 Hz), 8.40 (d, 1H, J=4.8 Hz).

Part 4:

1H-Pyrrolo[2,3-b]pyridine-4-carboxaldehyde: To a solution of (200 mg, 1.4 mmol) of 1H-Pyrrolo[2,3-b]pyridine-4-carbonitrile in THF (7 mL) at −78° C. under nitrogen was added Dibal-H (1.0 M in toluene, 3.07 mL, 3.07 mmol). The reaction mixture was stirred at −78° C. for 1 hr, warmed to 55° C. and stirred for additional 2 hr. One additional equivalent of DIBAL-H (1.4 mL, 1.4 mmol) was added and the mixture stirred at 55° C. for 2 hr. The mixture was cooled to 5° C., acidified with 2 M HCl and stirred for 15 min. The mixture was then neutralized with saturated $NaHCO_3$ (aq), extracted with $CH_2Cl_2$ (5×25 mL), washed with brine, dried over anhydrous sodium sulfate and concentrated in vacuo to give 1H-Pyrrolo[2,3-b]pyridine-4-carboxaldehyde (107 mg, 52%). MS (ES+): 146 [MH$^+$]. $^1$H NMR (DMSO-$d_6$, 400 MHz): δ 7.22 (d, 1H, J=3.6 Hz), 7.57 (d, 1H, J=4.8 Hz), 7.67 (d, 1H, J=2.4 Hz), 8.61 (d, 1H, J=5.2 Hz), 10.42 (s, 1H).

Part 5:

Methyl 3-[(1H-Pyrrolo[2,3-b]pyridin-4-ylmethyl)amino]thiophene-2-carboxylate: A solution of 3-aminothiophene-2-carboxylic acid methyl ester (110 mg, 0.701 mmol), and 1H-Pyrrolo[2,3-b]pyridine-4-carboxaldehyde (107 mg, 0.736 mmol) in $TFA/CH_2Cl_2$ (2 mL/2 mL) was stirred at 50° C. for 3 hr. The solution was cooled to 0° C. and triethylsilane (0.224 mL, 1.40 mmol) was added dropwise. The mixture was then stirred at 50° C. for 4 hr and treated with 2 N NaOH (aq)(to pH 6) and then saturated $NaHCO_3$ (aq)(to pH 8). The organic layer was separated and the aqueous layer was extracted with $CH_2Cl_2$ (3×10 mL). The organic extracts were combined, washed with brine, dried over anhydrous sodium sulfate and concentrated in vacuo. The residue was purified by chromatography over silica gel (gradient of 20% EtOAc/Hexanes to 70% EtOAc/Hexanes) to yield methyl 3-[(1H-Pyrrolo[2,3-b]pyridin-4-ylmethyl)amino]thiophene-2-carboxylate (98 mg, 49%). MS (ES+): 287 [MH$^+$]. $^1$H NMR (DMSO-$d_6$, 400 MHz): δ 3.75 (s, 3H), 4.84 (d, 2H, J=4.4 Hz), 6.74 (dd, 1H, J=2.8 Hz & 2.0 Hz), 6.70 (d, 1H, J=5.6 Hz), 7.01 (d, 1H, J=4.8 Hz), 7.51 (t, 1H, J=2.4 Hz), 7.61 (d, 1H, J=5.2 Hz), 8.18 (d, 1H, J=4.8 Hz).

Part 6:

N-(4-Trifluoromethoxy)phenyl-3-[(1H-pyrrolo[2,3-b]pyridin-4-ylmethyl)amino]thiophene-2-carboxamide: To a solution of 4-trifluoromethoxyaniline (0.381 mL, 1.74 mmol) in anhydrous toluene (5 mL) was added $AlMe_3$ (2.0 M in toluene, 0.520 mL, 1.4 mmol) and the solution was stirred at RT overnight. Methyl 3-[(1H-Pyrrolo[2,3-b]pyridin-4-ylmethyl)amino]thiophene-2-carboxylate (100 mg, 0.348 mmol) was added and the mixture was stirred at 130° C. overnight prior to cooling to room temperature and treatment with 15 mL of saturated $NaHCO_3$ (aq). After stirring for 1 hr the mixture was filtered, the filtrate layers separated, and the aqueous layer was extracted with $CH_2Cl_2$ (3×10 mL). The isolated solid was dissolved in 15 mL $CH_2Cl_2$ and all of the organic solutions (toluene and $CH_2Cl_2$) were combined, washed with brine, dried over anhydrous sodium sulfate and concentrated in vacuo. The residue was purified by chromatography over silica gel (gradient of 20% EtOAc/Hexanes to 50% EtOAc/Hexanes) to yield N-(4-Trifluoromethoxy)phenyl-3-[(1H-pyrrolo[2,3-b]pyridin-4-ylmethyl)amino]thiophene-2-carboxamide (93 mg, 62%). MS (ES+): 432 [MH$^+$]. $^1$H NMR (DMSO-$d_6$, 400 MHz): δ 4.81 (d, 2H, J=6.4 Hz), 6.62 (dd, 1H, J=3.6 & 1.6 Hz), 6.78 (d, 1H, J=5.6 Hz), 6.99 (d, 1H, J=4.8 Hz), 7.31 (d, 2H, J=8.8 Hz), 7.45 (dd, 1H, J=2.8 & 3.2 Hz), 7.59 (d, 1H, J=5.6 Hz, 1H), 7.79 (ddd, 2H, J=8.8, 3.2 & 2.0 Hz), 8.08 (t, 1H, J=6.4 Hz), 8.15 (d, 1H, J=4.8 Hz), 9.54 (s, 1H).

The following analogues were prepared using methyl 3-[(1H-Pyrrolo[2,3-b]pyridin-4-ylmethyl)amino]thiophene-2-carboxylate (EXAMPLE 13, part 5) and the appropriate aniline, according to the procedure described above for EXAMPLE 13, part 6.

EXAMPLE 14

N-(4-chlorophenyl)-3-[(1H-pyrrolo[2,3-b]pyridin-4-ylmethyl)amino]thiophene-2-carboxamide:

(5.1 mg, 4%). MS (ES+): 383 [MH$^+$].

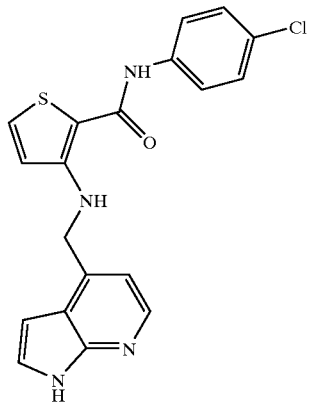

EXAMPLE 15

3-[(1H-pyrrolo[2,3-b]pyridin-4-ylmethyl)amino]-N-(2,2,3,3-tetrafluoro-2,3-dihydro-1,4-benzodioxin-6-yl)thiophene-2-carboxamide:

(19.4 mg, 16%). MS (ES+): 479 [MH$^+$].

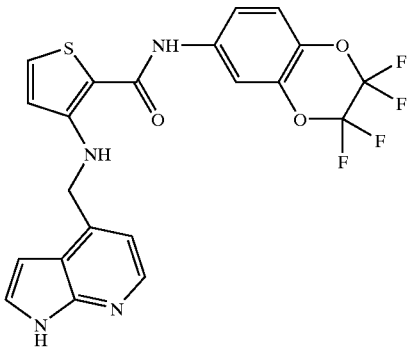

EXAMPLE 16

4-Methyl-N-(4-trifluoromethoxyphenyl)phenyl-3-[(quinolin-4-ylmethyl)amino]thiophene-2-carboxamide:

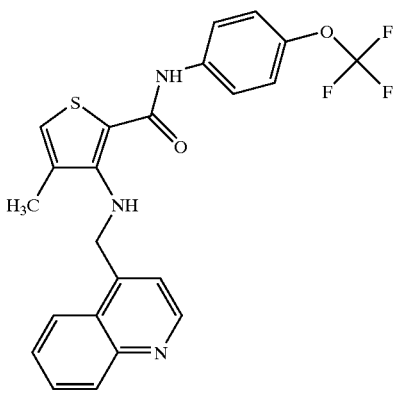

Prepared according to the procedure described for EXAMPLE 13, parts 5 and 6, utilizing methyl 3-amino-4-methylthiophene-2-carboxylate, quinoline-4-carboxaldehyde and 4-(trifluoromethoxy)aniline as starting materials. MS (ES+): 458 [MH$^+$], 459 [MH$^{2+}$]. $^1$H NMR (CDCl$_3$, 400 MHz): δ 2.15 (d, 3H, J=1.2 Hz), 5.01 (d, 2H, J=7.2 Hz), 6.98 (d, 1H, J=1.2 Hz), 7.17-7.24 (m, 3H), 7.51-7.54 (m, 3H), 7.58 (ddd, 1H, J=8.0, 6.4, 1.2 Hz), 7.74 (ddd, 1H, J=8.0, 6.8, 1.2 Hz), 7.86 (bs, 1H), 7.97 (dd, 1H, J=8.8, 0.8 Hz), 8.16 (d, 1H, J=8.0 Hz), 8.89 (d, 1H, J=4.8 Hz).

The following examples were prepared similarly, utilising the appropriate aniline in each case.

EXAMPLE 17

N-(4-chlorophenyl)-4-methyl-3-[(quinolin-4-ylmethyl)amino]thiophene-2-carboxamide:

MS (ES+): 408, 410 [MH$^+$]

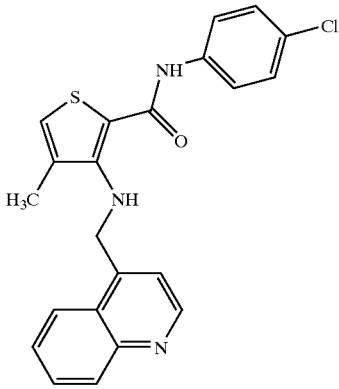

EXAMPLE 18

N-(4-bromo-3-methylphenyl)-4-methyl-3-[(quinolin-4-ylmethyl)amino]thiophene-2-carboxamide:

MS (ES+): 467, 469 [MH$^+$]

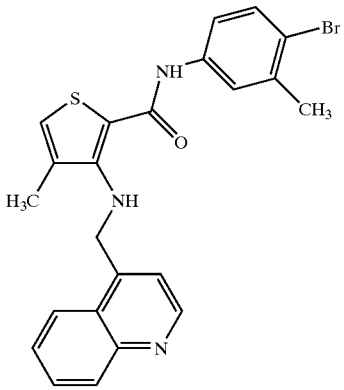

EXAMPLE 19

4-Methyl-3-[(quinolin-4-ylmethyl)amino]-N-(2,2,3,3-tetrafluoro-2,3-dihydro-1,4-benzodioxin-6-yl)thiophene-2-carboxamide:

MS (ES+): 503 [MH$^+$]

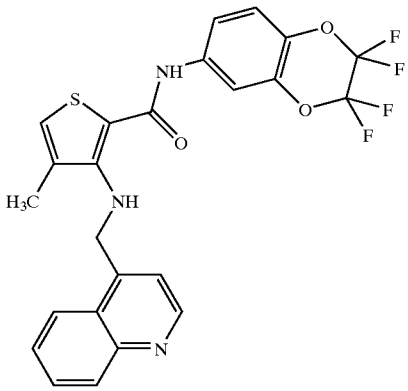

EXAMPLE 20

3-{[(1-oxidoquinolin-4-yl)methyl]amino}-N-[4-(trifluoromethoxy)phenyl]thiophene-2-carboxamide

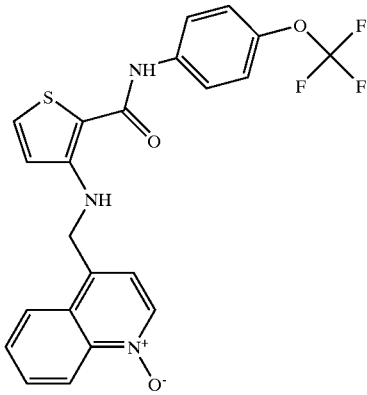

Part 1:

Quinolin-4-ylmethanol

A solution of quinoline-4-carbaldehyde (0.50 g, 3.24 mmol) dissolved in methanol (5 mL) was cooled to 0° C. Sodium borohydride (0.11 g, 2.91 mmol) was then added portion-wise. After 1 h of stirring at 0° C., 2M HCl (aq) was added drop-wise until pH~5. The methanol was then evaporated in vacuo and the aqueous phase was neutralized by addition of saturated aqueous $NaHCO_3$. The aqueous solution was extracted with $CH_2Cl_2$ (3×) and the combined organic extracts were washed with saturated $NaHCO_3$ (aq) and brine. The organic solution was dried over $Na_2SO_4$, filtered, and concentrated in vacuo to yield quinolin-4-ylmethanol as a yellow solid. MS (ES+): 160 [MH+]. $^1$H NMR ($CDCl_3$, 400 MHz): δ 2.41 (bs, 1H), 5.25 (bs, 2H), 7.55 (ddd, J=4.4, 1.2, 1.2 Hz, 1H), 7.58 (ddd, J=8.4, 7.2, 1.2 Hz, 1H), 7.73 (ddd, J=8.4, 6.8, 1.6 Hz, 1H), 7.97 (ddd, J=8.4, 1.2, 0.4 Hz, 1H), 8.14 (ddd, J=8.0, 1.2, 0.4 Hz, 1H), 8.90 (d, J=4.4 Hz, 1H).

Part 2:

(1-Oxidoquinolin-4-yl)methanol

To a solution of quinolin-4-ylmethanol (0.20 g, 1.26 mmol) dissolved in $CH_2Cl_2$ (10 mL), which was cooled to 0° C., was added m-chloroperbenzoic acid (57–86% w/w in $H_2O$, 0.50 mg) in one portion. The reaction was allowed to slowly warm to room temperature while stirring. After 17.5 h, the resulting solid was filtered and washed with $CH_2Cl_2$ to yield (1-oxidoquinolin-4-yl)methanol as a white solid. MS (ES+): 176 [MH+].

Part 3:

Quinoline-4-carbaldehyde 1-oxide

To a vigorously stirring suspension of (1-oxidoquinolin-4-yl)methanol (0.10 g, 0.57 mmol) in acetonitrile (10 mL) was added Dess-Martin periodinane (0.47 g, 0.63 mmol). After 1 h, 2M NaOH (aq, 2 mL) and ethyl acetate (105 mL) were added and the reaction was stirred for 5 min. The layers were then separated and the organic phase was washed with saturated $NaHCO_3$ (aq), brine, and dried over $MgSO_4$, filtered, and concentrated in vacuo to a light yellow solid. MS (ES+): 174 [MH+].

(This intermediate may also be prepared as described in *Heterocycles* (2003), 60(4), 953).

Part 4:

3-{[(1-Oxidoquinolin-4-yl)methyl]amino}-N-[4-(trifluoromethoxy)phenyl]thiophene-2-carboxamide A solution of quinoline-4-carboxaldehyde 1-oxide (0.12 g, 0.69 mmol), 3-amino-N-[4-(trifluoromethoxy)phenyl]thiophene-2-carboxamide (0.21 g, 0.69 mmol), dichloromethane (2 ml) and trifluoroacetic acid (2 ml) was heated at 50° C. for 2 hr, then cooled to room temperature, treated with triethylsilane (0.22 ml, 1.38 mmol) and stirred at 50° C. for another 2 h. After this time the mixture was diluted with water (40 ml), basified (pH 9) with 2M NaOH (aq) and extracted with ethyl acetate (3×20 ml). The extracts were washed with water (30 ml) and brine (30 ml), then dried ($MgSO_4$) and concentrated in vacuo to give crude product. This material was chromatographed over silica gel eluting with 15% acetonitrile/$CH_2Cl_2$, and the isolated product further purified by crystallization from acetonitrile to give 3-{[(1-oxidoquinolin-4-yl)methyl]amino}-N-[4-(trifluoromethoxy)phenyl]thiophene-2-carboxamide. MS (ES+): 460 [MH+]. $^1$H NMR (DMSO-$d_6$, 400 MHz): δ 5.00 (s, 2H), 6.87 (d, J=5.6 Hz, 1H), 7.25-7.40 (m, 3H), 7.65 (d, J=5.3 Hz, 1H), 7.73-7.91 (m, 4H), 8.0 (t, J=6.4 Hz, 1H), 8.30 (d, J=7.1 Hz, 1H), 8.56 (d, J=6.3 Hz, 1H), 8.61 (d, J=8.3 Hz, 1H), 9.60 (s, 1H).

What is claimed is:

1. A compound represented by Formula (I):

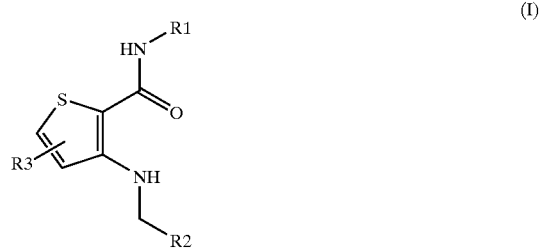

or a pharmaceutically acceptable salt or N-oxide thereof, wherein

R1 is

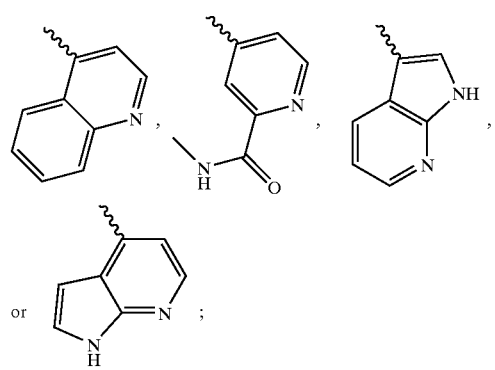

R2 is

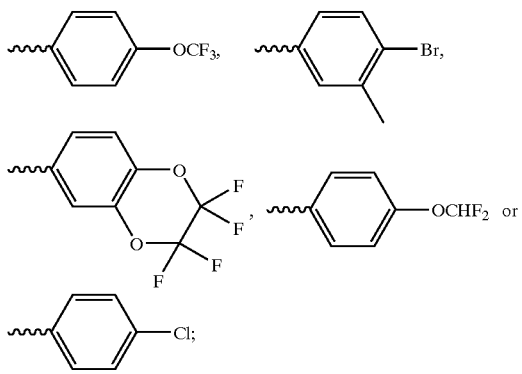

and
R3 is $C_{0-4}$alkyl.

2. The compound according to claim 1, or a pharmaceutically acceptable salt or N-oxide thereof, wherein R2 is

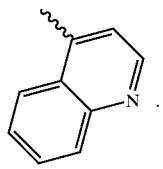.

3. The compound according to claim 1, or a pharmaceutically acceptable salt or N-oxide thereof, wherein R2 is

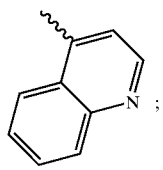;

and R3 is hydrogen.

4. The compound according to claim 1, or a pharmaceutically acceptable salt or N-oxide thereof, wherein R2 is

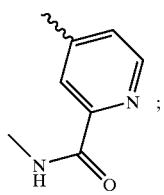;

5. The compound according to claim 1, or a pharmaceutically acceptable salt or N-oxide thereof, wherein R2 is

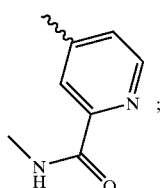;

and R3 is hydrogen.

6. The compound according to claim 1, or a pharmaceutically acceptable salt or N-oxide thereof, wherein R2 is

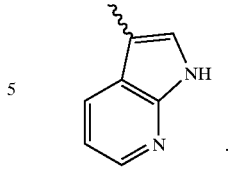.

7. The compound according to claim 1, or a pharmaceutically acceptable salt or N-oxide thereof, wherein R2 is

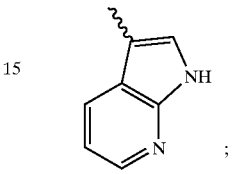;

and R3 is $C_{0-4}$alkyl.

8. The compound according to claim 1, or a pharmaceutically acceptable salt or N-oxide thereof, wherein R2 is

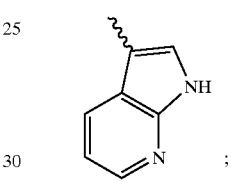;

and R3 is hydrogen.

9. The compound according to claim 1, or a pharmaceutically acceptable salt or N-oxide thereof, wherein R2 is

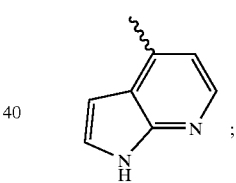;

and R3 is $C_{0-4}$alkyl.

10. A composition comprising a compound according to claim 1, or a pharmaceutically acceptable salt or N-oxide thereof, and a pharmaceutically acceptable carrier.

11. A composition comprising a compound according to claim 1, or a pharmaceutically acceptable salt or N-oxide thereof; and
    an anti-neoplastic, anti-tumor, anti-angiogenic, or chemotherapeutic agent.

12. A composition comprising a compound according to claim 1, or a pharmaceutically acceptable salt or N-oxide thereof, and a cytotoxic cancer therapeutic agent.

13. A composition comprising a compound according to claim 1, or a pharmaceutically acceptable salt or N-oxide thereof, and an angiogenesis inhibiting cancer therapeutic agent.

14. A compound consisting of
    N-(4-trifluoromethoxyphenyl) 3-[(quinolin-4-ylmethyl)amino]thiophene-2-carboxamide;
    N-(4-bromo-3-methylphenyl) 3-[(quinolin-4-ylmethyl)amino]thiophene-2-carboxamide;
    N-(2,2,3,3-tetrafluorobenzodioxan-6-yl) 3-[(quinolin-4-ylmethyl)amino]thiophene-2-carboxamide;

N-(4-chlorophenyl) 3-[(quinolin-4-ylmethyl)amino]thiophene-2-carboxamide;

4-{[2-(4-bromo-3-methylphenylcarbamoyl)thiophen-3-ylamino]methyl}pyridine-2-carboxylic acid methylamide;

4-{[2-(2,2,3,3-tetrafluorobenzodioxan-6-ylcarbamoyl)thiophen-3-ylamino]methyl}pyridine-2-carboxylic acid methylamide;

4-{[2-(4-chlorophenylcarbamoyl)thiophen-3-ylamino]methyl}pyridine-2-carboxylic acid methylamide;

N-(4-chlorophenyl) 3-[(1H-pyrrolo[2,3-b]pyridin-3-ylmethyl)amino]thiophene-2-carboxamide;

N-(4-bromo-3-methylphenyl) 3-[(1H-pyrrolo[2,3-b]pyridin-3-ylmethyl)amino]thiophene-2-carboxamide;

N-(2,2,3,3-tetrafluorobenzodioxan-6-yl) 3-[(1H-pyrrolo[2,3-b]pyridin-3-ylmethyl)amino]thiophene-2-carboxamide;

N-{[2-(4-trifluoromethoxyphenylcarbamoyl)thiophen-3-ylamino]methyl}pyridine-2-carboxylic acid methylamide; and N-(4-Trifluoromethoxy)phenyl-3-[(1H-pyrrolo[2,3-b]pyridin-4-ylmethyl)amino]thiophene-2-carboxamide;

N-(4-chlorophenyl)-3-[(1H-pyrrolo[2,3-b]pyridin-4-ylmethyl)amino]thiophene-2-carboxamide;

3-[(1H-pyrrolo[2,3-b]pyridin-4-ylmethyl)amino]-N-(2,2,3,3-tetrafluoro-2,3-dihydro-1,4-benzodioxin-6-yl)thiophene-2-carboxamide;

4-Methyl-N-(4-trifluoromethoxyphenyl)phenyl-3-[(quinolin-4-ylmethyl)amino]thiophene-2-carboxamide;

N-(4-chlorophenyl)-4-methyl-3-[(quinolin-4-ylmethyl)amino]thiophene-2-carboxamide;

N-(4-bromo-3-methylphenyl)-4-methyl-3-[(quinolin-4-ylmethyl)amino]thiophene-2-carboxamide;

4-Methyl-3-[(quinolin-4-ylmethyl)amino]-N-(2,2,3,3-tetrafluoro-2,3-dihydro-1,4-benzodioxin-6-yl)thiophene-2-carboxamide;

3-{[(1-oxidoquinolin-4-yl)methyl]amino}-N-[4-(trifluoromethoxy)phenyl]thiophene-2-carboxamide or a pharmaceutically acceptable salt, or N-oxide, thereof.

15. A method of treatment of hyperproliferative disorder comprising a step of administering an effective amount of the compound according to claim 1 wherein the hyperproliferative disorder is selected from the group consisting of breast cancer, head cancer, neck cancer, gastrointestinal cancer, leukemia, ovarian, bronchial, lunch or pancreatic cancer.

16. The method of claim 15 wherein the hyperproliferative disorder is sinonasal natural killer/T-cell lymphoma, testicular cancer (seminoma), thyroid carcinoma, malignant melanoma, adenoid cystic carcinoma, angiosarcoma, anaplastic large cell lymphoma, endometrial carcinoma, or prostate carcinoma.

* * * * *

UNITED STATES PATENT AND TRADEMARK OFFICE
CERTIFICATE OF CORRECTION

PATENT NO. : 6,949,563 B2
DATED : September 27, 2005
INVENTOR(S) : Graham Michael Wynne et al.

It is certified that error appears in the above-identified patent and that said Letters Patent is hereby corrected as shown below:

Column 34,
Line 20, "lunch" should be -- lung --.

Signed and Sealed this

Twenty-seventh Day of December, 2005

JON W. DUDAS
*Director of the United States Patent and Trademark Office*

UNITED STATES PATENT AND TRADEMARK OFFICE
CERTIFICATE OF CORRECTION

PATENT NO. : 6,949,563 B2
APPLICATION NO. : 10/752342
DATED : September 27, 2005
INVENTOR(S) : Wynne et al.

It is certified that error appears in the above-identified patent and that said Letters Patent is hereby corrected as shown below:

In column 30, lines 53-65 (Claim 1),

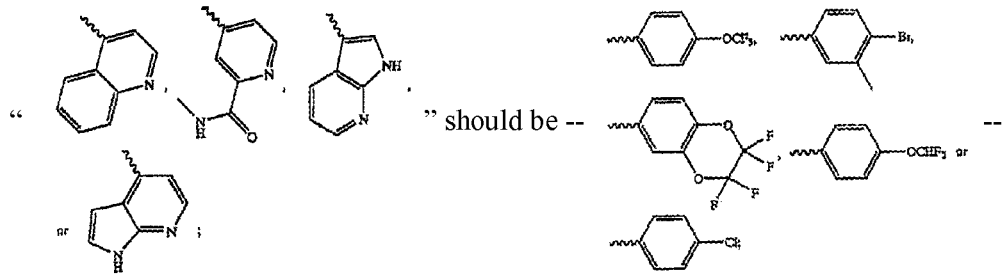

In column 31, lines 3-17 (Claim 1),

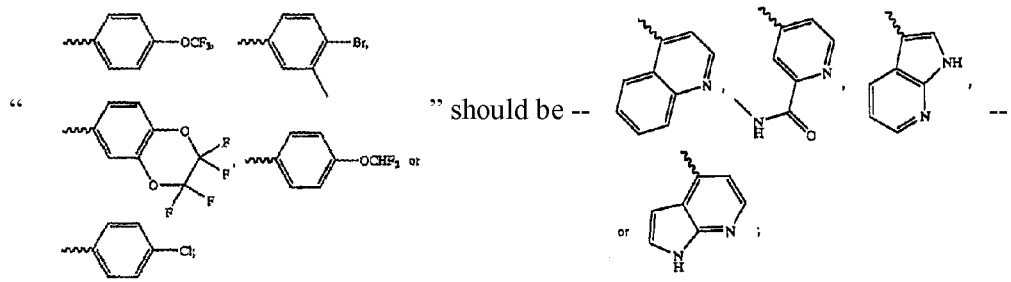

Signed and Sealed this

Eighteenth Day of November, 2008

JON W. DUDAS
*Director of the United States Patent and Trademark Office*